US011319579B2

(12) United States Patent
Su'etsugu et al.

(10) Patent No.: US 11,319,579 B2
(45) Date of Patent: *May 3, 2022

(54) METHOD OF AMPLIFYING CIRCULAR DNA

(71) Applicant: OriCiro Genomics, Inc., Tokyo (JP)

(72) Inventors: Masayuki Su'etsugu, Tokyo (JP); Hiroko Kobayashi, Tokyo (JP)

(73) Assignee: OriCiro Genomics, Inc., Tokyo (JP)

( * ) Notice: Subject to any disclaimer, the term of this patent is extended or adjusted under 35 U.S.C. 154(b) by 165 days.

This patent is subject to a terminal disclaimer.

(21) Appl. No.: 16/371,766

(22) Filed: Apr. 1, 2019

(65) Prior Publication Data

US 2019/0249236 A1 Aug. 15, 2019

Related U.S. Application Data

(62) Division of application No. 15/527,560, filed as application No. PCT/JP2015/082356 on Nov. 18, 2015, now Pat. No. 10,301,672.

(30) Foreign Application Priority Data

Nov. 18, 2014 (JP) .................................. 2014-233563

(51) Int. Cl.
| | | |
|---|---|---|
| C12Q 1/6844 | (2018.01) | |
| C12Q 1/6853 | (2018.01) | |
| C12Q 1/686 | (2018.01) | |
| C12N 15/09 | (2006.01) | |
| C12N 9/00 | (2006.01) | |
| C12N 9/12 | (2006.01) | |
| C12N 9/16 | (2006.01) | |
| C12N 9/90 | (2006.01) | |
| C12P 19/34 | (2006.01) | |
| C12N 15/00 | (2006.01) | |

(52) U.S. Cl.
CPC ............ *C12Q 1/6846* (2013.01); *C12N 9/00* (2013.01); *C12N 9/12* (2013.01); *C12N 9/16* (2013.01); *C12N 9/90* (2013.01); *C12N 15/09* (2013.01); *C12P 19/34* (2013.01); *C12Q 1/686* (2013.01); *C12Q 1/6853* (2013.01); *C12N 15/00* (2013.01)

(58) Field of Classification Search
CPC .... C12Q 1/6846; C12Q 1/6853; C12Q 1/686; C12Q 2525/307; C12N 9/00; C12N 9/12; C12N 9/16; C12N 9/90; C12N 15/09; C12N 15/00; C12P 19/34
See application file for complete search history.

(56) References Cited

U.S. PATENT DOCUMENTS

| | | |
|---|---|---|
| 6,340,476 B1 | 1/2002 | Midha et al. |
| 6,506,581 B1 | 1/2003 | Fleischmann et al. |
| 10,301,672 B2 | 5/2019 | Su'etsugu et al. |
| 2010/0028862 A1* | 2/2010 | Jarvis ..................... C07K 14/21 435/5 |
| 2017/0321263 A1 | 11/2017 | Su'etsugu et al. |
| 2019/0249236 A1 | 8/2019 | Su'etsugu et al. |
| 2019/0276883 A1 | 9/2019 | Su'etsugu et al. |
| 2020/0115727 A1 | 4/2020 | Su'etsugu et al. |

FOREIGN PATENT DOCUMENTS

| | | |
|---|---|---|
| EP | 1916311 A1 | 4/2008 |
| EP | 3222717 A1 | 9/2017 |
| JP | 2005229950 A | 9/2005 |
| JP | 2008-161182 A | 7/2008 |
| JP | 2012-501173 A | 1/2012 |
| WO | 199523875 A1 | 9/1995 |
| WO | 200078977 A1 | 12/2000 |
| WO | 2010026099 A1 | 3/2010 |
| WO | 2016080424 A1 | 5/2016 |

OTHER PUBLICATIONS

Hiasa, H. et al. (1994). "Primase Couples Leading- and Lagging-strand DNA." The Journal of Biological Chemistry 269(8): 6058-6063.
Funnell, B.E. et al. (Apr. 25, 1986). "Complete enzymatic replication of plasmids containing the origin of the *Escherichia coli* chromosome," *J Biol Chem* 261 (12):5616-5624.
Hiasa, H. et al. (Jan. 21, 1994). "Decatenating activity of *Escherichia coli* DNAgyrase and topoisomerases I and III during oriC and pBR322 DNA replication in vitro," *J Biol Chem* 269(3):2093-2099.
Hiasa, H. et al. (Dec. 23, 1994). "Topoisomerase III, but not topoisomerase I, can support nascent chain elongation during theta-type DNA replication," *J Biol Chem* 269(51):32655-32659.
International Search Report dated Feb. 16, 2016, for PCT Application No. PCT/JP2015082356, filed Nov. 18, 2015, 2 pages.
Chen, Z. et al. (Dec. 1, 1998). "Amplification of closed circular DNA in vitro," *Nucleic Acids Res* 26(23):1126-1127.
Su'etsugu, M. et al. (Nov. 16, 2017). "Exponential propagation of large circular DNA by reconstitution of a chromosome-replication cycle," *Nucleic Acids Res* 45(20):11525-11534.
Extended European Search Report dated Mar. 27, 2018, for EP Application No. 15860324.1, 9 pages.

(Continued)

*Primary Examiner* — David C Thomas
(74) *Attorney, Agent, or Firm* — Muriel Liberto; Mintz Levin Cohn Ferris Glovsky and Popeo, P.C.

(57) ABSTRACT

The present invention provides a method for easily and exponentially amplifying circular DNA, particularly long chain circular DNA, in a cell-free system. Specifically, the present invention provides a method for amplifying circular DNA in which circular DNA having a replication origin sequence (origin of chromosome (oriC)) is mixed with a reaction solution containing the following enzyme groups to form a reaction mixture, which is then reacted under an isothermal condition, the enzyme groups being:
(1) a first enzyme group that catalyzes replication of circular DNA;
(2) a second enzyme group that catalyzes an Okazaki fragment maturation and synthesizes two sister circular DNAs constituting a catenane and
(3) a third enzyme group that catalyzes a separation of two sister circular DNAs.

15 Claims, 8 Drawing Sheets

(56) References Cited

OTHER PUBLICATIONS

Suski, C. (Jun. 20, 2008). "Resolution of converging replication forks by RecQ and topoisomerase III." *Mol. Cell.* 30(6):779-789.
Gusev, Y. (Jul. 2001). "Rolling circle amplification: a new approach to increase sensitivity for immunohistochemistry and flow cytometry." *Amer. J. Pathol.* 159(1):63-69.
Hiasa,H. (Oct. 28, 1994). "Tus prevents overreplication of OriC plasmid Dna." *J. Biol. Chem.* 269(43):26959-26968.
Chao, R. et al. (2015). "Recent advances in DNA assembly technologies." FEMS Yeast Research 15:1-9.
Extended European Search Report dated Dec. 16, 2019 for European Application No. 17799415.9, filed on May 17, 2017. 5 pages.
Fakrrudin, M. et al. (2013). "Nucleic acid amplification: Alternative methods of polymerase chain reaction." Journal of Pharmacy and Bioallied Sciences 5(4): 245-252.
Funnell, B. et al. (Apr. 25, 1986). "Complete enzymatic replication of plasmids containing the origin of the *Escherichia coli* chromosome," J Biol Chem 261(12):5616-5624.
Gusev, Y. et al. (2001). "Rolling circle amplification: A new approach to increase sensitivity for immunohistochemistry and flow cytometry." American Journal of Pathology 159(1):63-69.
Hiasa, H. et al. (1994). "Topoisomerase IV can support OriC DNA replication in vitro." The Journal of Biological Chemistry 269(23):16371-16375.
Hiasa, H. et al. (1994). "Tus prevents overreplication of oriC plasmid DNA." The Journal of Biological Chemistry 269(43):26959-26968.
Hiasa, H. et al. (Jan. 21, 1994). "Decatenating activity of *Escherichia coli* DNA gyrase and topoisomerases I and III during oriC and pBR322 DNA replication in vitro," The Journal of Biological Chemistry 269(3):2093-2099.
Hiasa, H. et al. (1994). "Topoisomerase III, but not topoisomerase I, can support nascent chain elongation during theta-type DNA replication." The Journal of Biological Chemistry 269(51):32655-32659.
International Search Report dated May 29, 2018 for International Application No. PCT/JP2018/007485, filed on Feb. 28, 2018. 2 pages.
International Search Report dated Aug. 15, 2017 for International Application No. PCT/JP2017/018472, filed May 17, 2017. 5 pages.
International Search Report dated Feb. 16, 2016 for International Application No. PCT/JP2015/082356, filed Nov. 18, 2015. 2 pages.
Kaguni, J. et al. (1984). "Replication initiated at the origin (OriC) of the *E. coli* chromosome reconstituted with purified enzymes." Cell 38:183-190.
Peng, H. et al. (1993). "Decatenation activity of topoisomerase IV during oriC and pBR322 DNA replication in vitro." Proceedings of the National Academy of Sciences USA 90:8571-8575.
Suski, C. et al. (2008). "Resolution of converging replication forks by RecQ and topoisomerase III." Molecular Cell 30 (6):779-789.
Tsuge, K. et al. (2003). "One step assembly of multiple DNA fragments with a designed order and orientation in *Bacillus subtillis* plasmid." Nucleic Acids Research vol. 31, No. 21. 8 pages.
Bailey et al. (2015) "Termination of DNA Replication Forks: Breaking up is hard to do", Nucleus, 6(3): 187-196.
C.Y.IP et al. (Dec. 1, 2003) "Decatenation of DNA Circles by FtsK-dependent Xer site-specific Recombination", The EMBO Journal, , 22(23): 6399-6407.
Beattiet al. (Jun. 5, 2015) "A Replisome's Journey Through The Bacterial Chromosome", Frontiers in Microbiology, 6:562.
Kuzminov A. (Dec. 1999) "Recombinational Repair Of DNA Damage In *Escherichia coli* And Bacteriophage Lambda", Microbiology and Molecular Biology Reviews, 63(4):751-813.

* cited by examiner

METHOD OF AMPLIFYING CIRCULAR DNA

CROSS-REFERENCE TO RELATED APPLICATIONS

The present application is a divisional of U.S. patent application Ser. No. 15/527,560 filed on May 17, 2017, now U.S. Pat. No. 10,301,672 issued on May 28, 2019, which is a U.S. national stage application, under 35 U.S.C. § 371, of International Application No. PCT/JP2015/082356 filed on Nov. 18, 2015, which claims priority to Japanese Application No. 2014-233563 filed on Nov. 18, 2014, the contents of which are hereby fully incorporated by reference.

TECHNICAL FIELD

The present invention relates to a method for amplifying circular DNA. More specifically, the present invention relates to a method that allows exponential amplification of circular DNA in a cell-free system.

BACKGROUND ART

The DNA cloning technology on which biotechnological development was based is a technique for amplifying circular DNA that had been prepared by cutting and pasting DNA fragments as plasmid in cells of *E. coli*, etc. A use of a DNA cloning technology that uses cells to amplify circular DNA necessitates troublesome procedures such as cell cultivation, extraction/purification of amplified products and the like. Also, the environment for experimenting such DNA cloning is limited, since it is necessary to prepare genetically modified organisms to perform DNA cloning that uses cells.

A common method used for amplifying DNA in vitro is polymerase chain reaction (PCR). However, an in vitro DNA amplification using PCR does not allow circular DNA to be amplified as it is. In vitro amplification methods of circular DNA include the rolling circle amplification (RCA) (Non-Patent Document 1, Patent Document 1, Patent Document 2, Patent Document 3). However, if circular DNA is to be amplified using the rolling circle amplification, a primer specific to the target DNA would need to be designed each time. Furthermore, the amplification product that directly results from the rolling circle amplification is a linear DNA, so it would be necessary to perform an additional cyclization step to cyclize the obtained amplification product, such as incubating with a recombinant enzyme. Another reported method is a method of obtaining a monomer replication product by separating a minichromosome of *E. coli* (oriC circular DNA) after it had been replicated (Non-Patent Document 2), but this method amplifies only circular DNA of up to about 6 kbp. There is also a report of rearranging replication of minichromosomes of *E. coli* using a group of purified enzymes derived from *E. coli* (Non-Patent Document 3), but no method is known for exponentially amplifying the entire long circular DNA in vitro by repeating replication cycles in a single test tube.

As shown above, amplification of circular DNA using the conventional in vitro DNA amplification was disadvantageous in that it required primers to be bonded with the template DNA, produced linear DNA as the amplification product, and limited the size of DNA that can be amplified to within a few kb.

Methods such as the SLIC method and the Gibson Assembly method have been proposed as technologies to prepare long DNAs, but in either case, the final preparation of the long chain circular DNA can only be performed by using cells (Non-Patent Document 4). A method using *Bacillus subtilis* has been reported as a method for preparing long chain circular DNA by using cells (Non-Patent Document 5).

CITATION LIST

Patent Documents

Patent Document 1: Japanese unexamined patent publication No. 2005-229950

Patent Document 2: Japanese unexamined patent publication No. 2008-161182

Patent Document 3 Japanese unexamined patent publication No. 2012-501173

Non-Patent Documents

Non-Patent Document 1: Fakruddin M et al., J Pharm Bioallied Sci. 2013, 5: 245-252

Non-Patent Document 2: Peng H & Marians K J. PNAS. 1993, 90: 8571-8575

Non-Patent Document 3: Kaguni J M & Kornberg A. Cell. 1984, 38:183-90

Non-Patent Document 4: Chao R et al., FEMS YEAST Res. 2014

Non-Patent Document 5: Tsuge et al., Nucleic Acids Res. 2003, 31:e133

SUMMARY OF INVENTION

Technical Problem

The object of the present invention is to provide a method for easily and exponentially amplifying circular DNA, especially long chain circular DNA, in a cell-free system.

Solution to Problem

The present inventors performed extensive studies to solve the above problem and found that the cycle of "initiation of replication (unwinding of DNA double strand)/elongation (progress of replication fork)/separation of replicated sister DNAs (Decatenation)" is repeated and exponential amplification of circular DNA is provided when circular DNA having a replication origin sequence (origin of chromosome (oriC)) is mixed with a reaction solution containing the following enzyme groups to form a reaction mixture, which is then reacted under an isothermal condition, the enzyme groups being:

(1) a first enzyme group that catalyzes replication of circular DNA;

(2) a second enzyme group that catalyzes an Okazaki fragment maturation and synthesizes two sister circular DNAs constituting a catenane; and (3) a third enzyme group that catalyzes a separation of two sister circular DNAs.

In other words, the present invention encompasses the following aspect without being limited thereby.

[1] A method for amplifying circular DNA comprising the steps of:
(1) forming a reaction mixture composed of a reaction solution containing
a first enzyme group that catalyzes replication of circular DNA;
a second enzyme group that catalyzes an Okazaki fragment maturation and synthesizes two sister circular DNAs constituting a catenane; and
a third enzyme group that catalyzes a separation of two sister circular DNAs and circular DNA that constitutes a template, wherein the circular DNA includes a replication origin sequence (origin of chromosome (oriC)) that can bind to an enzyme having DnaA activity; and
(2) retaining temperature of the reaction mixture formed in (1) under an isothermal condition.
[2] The method according to [1], wherein
the first enzyme group that catalyzes replication of circular DNA is a combination of an enzyme having DnaA activity, one or more types of nucleoid protein, an enzyme or enzyme group having DNA gyrase activity, single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III activity;
the second enzyme group that catalyzes an Okazaki fragment maturation and synthesizes two sister circular DNAs constituting a catenane is a combination of an enzyme having RNaseH activity, an enzyme having DNA polymerase I activity, and an enzyme having DNA ligase activity; and
the third enzyme group that catalyzes a separation of two sister circular DNAs is a combination of an enzyme having topoisomerase IV activity, an enzyme having topoisomerase III activity, and an enzyme having RecQ activity.
[3] The method according to [2], wherein a replication origin sequence that can bind to an enzyme having DnaA activity is a replication origin sequence of *E. coli*.
[4] The method according to either [2] or [3], wherein a size of circular DNA is 50 kb or greater.
[5] The method according to any one of [2] to [4], wherein the one or more nucleoid protein is a combination of IhfA and IhfB.
[6] The method according to any one of [2] to [5], wherein the enzyme or enzyme group having DNA gyrase activity is a combination of GyrA and GyrB.
[7] The method according to any one of [2] to [6], wherein the enzyme having DNA helicase activity is DnaB helicase.
[8] The method according to any one of [2] to [7], wherein the enzyme having DNA helicase loader activity is DnaC helicase loader.
[9] The method according to any one of [2] to [8], wherein the enzyme having DNA primase activity is DnaG primase.
[10] The method according to any one of [2] to [9], wherein the enzyme having DNA clamp activity is DnaN clamp.
[11] The method according to any one of [2] to [10], wherein the enzyme or enzyme group having DNA polymerase III activity is a combination of DnaX, HolA, HolB, HolC, HolD, DnaE, DnaQ, and HolE.
[12] The method according to any one of [2] to [11], wherein the enzyme having DnaA activity, the one or more types of nucleoid protein, the enzyme or enzyme group having DNA gyrase activity, the single-strand binding protein (SSB), the enzyme having DNA helicase activity, the enzyme having DNA helicase loader activity, the enzyme having DNA primase activity, the enzyme having DNA clamp activity, the enzyme or enzyme group having DNA polymerase III activity, the enzyme having RNaseH activity, the enzyme having DNA polymerase I activity, the enzyme having DNA ligase activity, the enzyme having topoisomerase IV activity, the enzyme having topoisomerase III activity, and the enzyme having RecQ activity are derived from *E. coli*.
[13] The method according to any one of [1] to [12], wherein the reaction solution of step (1) further contains a constituent that prevents or reduces development of a byproduct.
[14] The method according to any one of [1] to [13], wherein the isothermal condition in step (2) is a constant temperature in a range of 25° C. to 50° C.
[15] A composition for amplifying circular DNA comprising
a first enzyme group that catalyzes replication of circular DNA;
a second enzyme group that catalyzes an Okazaki fragment maturation and synthesizes two sister circular DNAs constituting a catenane; and
a third enzyme group that catalyzes a separation of two sister circular DNAs.
[16] A composition according to [15], wherein
the first enzyme group that catalyzes replication of circular DNA is a combination of an enzyme having DnaA activity, one or more types of nucleoid protein, an enzyme or enzyme group having DNA gyrase activity, single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III activity;
the second enzyme group that catalyzes an Okazaki fragment maturation and synthesizes two sister circular DNAs constituting a catenane is a combination of an enzyme having RNaseH activity, an enzyme having DNA polymerase I activity, and an enzyme having DNA ligase activity; and
the third enzyme group that catalyzes a separation of two sister circular DNAs is a combination of an enzyme having topoisomerase IV activity, an enzyme having topoisomerase III activity, and an enzyme having RecQ activity.
[17] A kit for amplifying circular DNA comprising
a first enzyme group that catalyzes replication of circular DNA;
a second enzyme group that catalyzes an Okazaki fragment maturation and synthesizes two sister circular DNAs constituting a catenane; and
a third enzyme group that catalyzes a separation of two sister circular DNAs
[18] The kit according to [17], wherein
the first enzyme group that catalyzes replication of circular DNA is a combination of an enzyme having DnaA activity, one or more types of nucleoid protein, an enzyme or enzyme group having DNA gyrase activity, single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III activity;
the second enzyme group that catalyzes an Okazaki fragment maturation and synthesizes two sister circular DNAs constituting a catenane is a combination of an enzyme having RNaseH activity, an enzyme having DNA polymerase I activity, and an enzyme having DNA ligase activity; and
the third enzyme group that catalyzes a separation of two sister circular DNAs is a combination of an enzyme having topoisomerase IV activity, an enzyme having topoisomerase III activity, and an enzyme having RecQ activity.

Advantageous Effects of Invention

The present invention provides a method for easily and exponentially amplifying circular DNA, especially long chain circular DNA, without using *E. coli* cells or plasmid vectors. The present invention frees the circular DNA amplification from temperature regulation cycles and primers, and enables amplification of long chain circular DNA that exceeds 200 kb. Furthermore, the amplification product obtained by the present invention is a copy that maintains the circular structure of the original template. By adding DNA fragments to the reaction system after the DNA fragments had been ligated, the present invention also enables specific amplification of only the DNA that was cyclized by ligation.

BRIEF DESCRIPTION OF DRAWINGS

FIG. 4a shows the result of the amplification product at each reaction time in a case in which a long chain circular DNA of 200 kb (15 pM, 20 ng) was used as a template. FIG. 4b shows the result of the amplification product 3 h. after reaction in a case in which long chain circular DNAs of 80 kb (15 pM, 8 ng) and 200 kb (5 pM, 6.7 ng) were used as templates.

FIG. 6a shows the detection result of the amplification product in a case in which a circular DNA of 9.6 kb was used as a template, the detection result obtained by using SyberGreen after subjecting the product to agarose electrophoresis. FIG. 6b is a graph that depicts the result of the amplification level by quantifying the amount of DNA of the amplification product by using the PicoGreen method or by transforming *E. coli*.

FIG. 8a is a scheme of a dilution of a circular DNA mixture. FIG. 8b shows the detection result of the amplification product in a case in which a diluted mixture of circular DNA was amplified, the detection result obtained by using SyberGreen after subjecting the product to agarose electrophoresis.

FIG. 9a is a scheme of the experiment process. FIG. 9b shows the result in a case in which a passage amplification was repeated 10 times by diluting the DNA product after amplification to form a new reaction solution, then subjecting the solution to amplification again.

DESCRIPTION OF EMBODIMENTS

<Circular DNA>

Figure 1:
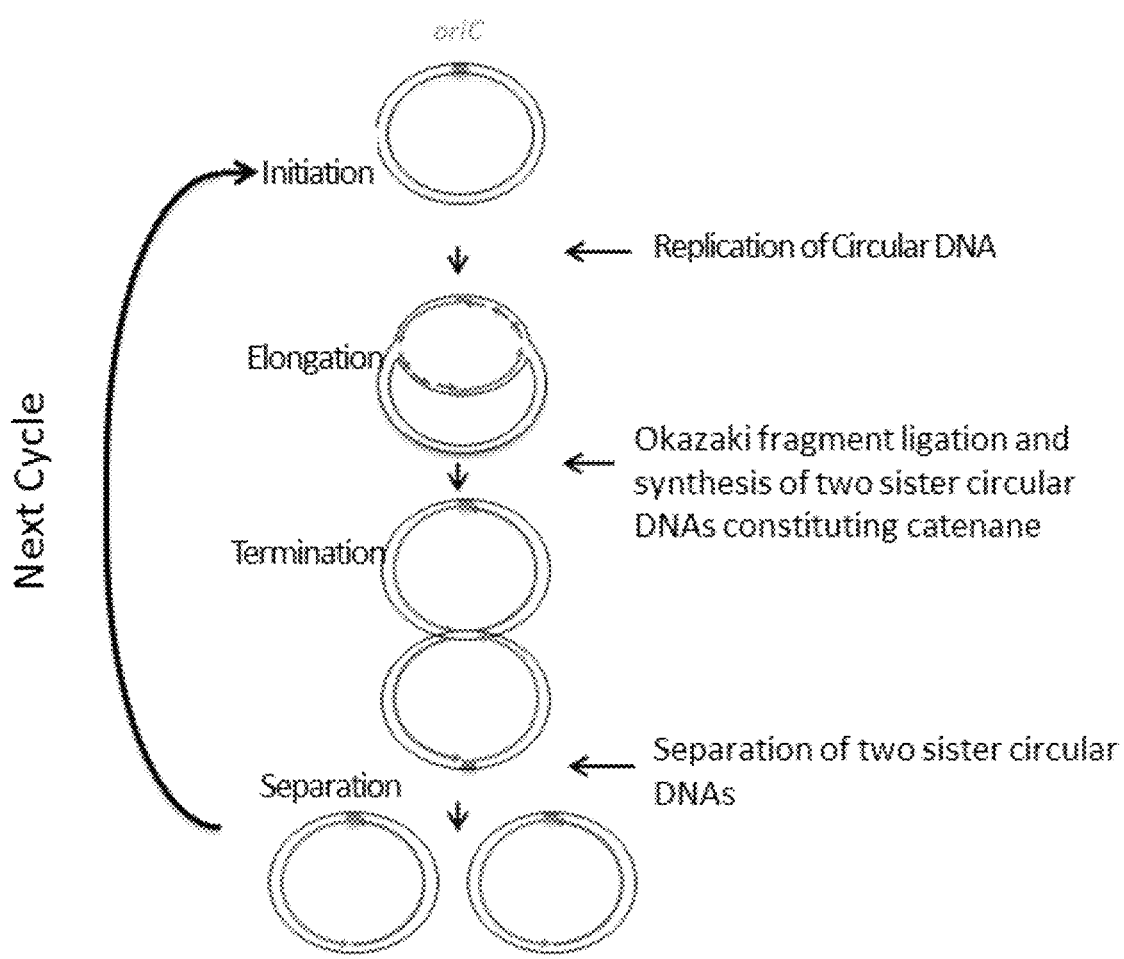
FIG. 1 shows a model of the replication cycle of the present invention.

The circular DNA that is used as the template is preferably a double-strand. The circular DNA used as the template is not particularly limited as long as it includes a replication origin sequence (origin of chromosome (oriC)) that can bind to an enzyme having DnaA activity, and examples include natural circular DNA such as a circular chromosome of microorganisms, circular DNA created by ligating natural circular DNA that had been cut off by enzyme processing, etc. with another DNA fragment and cyclizing the ligated product, and circular DNA that had been artificially synthesized altogether. With regards to replication origin sequences (origin of chromosome (oriC)) that can bind to an enzyme having DnaA activity (may be referred to hereinafter, simply as "replication origin sequence"), publicly known replication origin sequences existing in bacterium, such as *E. coli, Bacillus subtilis*, etc., may be obtained from a public database such as NCBI (http://www.ncbi.nlm.nih.gov/). Or else, the replication origin sequence may be obtained by cloning a DNA fragment that can bind to an enzyme having DnaA activity and analyzing its base sequence.

The circular DNA that is to be used as a template in the present invention may be circular DNA containing a replication origin sequence from the beginning, or circular DNA originally lacking a replication origin sequence but later incorporating a replication origin sequence.

The circular DNA that is used as a template in the present invention may include marker gene sequences that are resistant to drugs, such as kanamycin, ampicillin, tetracycline, etc. according to the purpose.

Furthermore, the circular DNA that is used as a template in the present invention may be in a purified state, or it may be in a form of a suspension of fungus body extraction including circular DNA. A single type of circular DNA may be used as a template, but it is also possible to use a mixture of several types of circular DNAs, such as a DNA library, in one test tube as a template.

There is no limit to the amount of template DNA to be used in a single reaction, and a single circular DNA molecule may be used per reaction.

There is no limit to the length of circular DNA used as a template in the present invention, and the length may be 1 kb (1,000 base length) or longer, 5 kb (5,000 base length) or longer, 8 kb (8,000 base length) or longer, 10 kb (10,000 base length) or longer, 50 kb (50,000 base length) or longer, 100 kb (100,000 base length) or longer, 200 kb (200,000 base length) or longer, 500 kb (500,000 base length) or longer, 1000 kb (1,000,000 base length) or longer, or 2000 kb (2,000,000 base length) or longer.

In the present invention, the above circular DNAs may be used as templates, and they may be amplified to at least 10 folds, 50 folds, 100 folds, 200 folds, 500 folds, 1,000 folds, 2,000 folds, 3,000 folds, 4,000 folds, 5,000 folds or 10,000 folds.

<First, Second and Third Enzyme Groups>

The present invention relates to subjecting a reaction mixture to an isothermal reaction, in which the reaction mixture was composed by mixing circular DNA having a replication origin sequence (origin of chromosome (oriC)) with a reaction solution containing the following enzyme groups:

(1) a first enzyme group that catalyzes replication of circular DNA;
(2) a second enzyme group that catalyzes an Okazaki fragment maturation and synthesizes two sister circular DNAs constituting a catenane; and
(3) a third enzyme group that catalyzes a separation of two sister circular DNAs.

Although not limited theoretically, the present invention repeats the replication cycle as shown in FIG. 1, and exponentially amplifies circular DNA.

<(1) First Enzyme Group that Catalyzes Replication of Circular DNA>

An example of a first enzyme group that catalyzes replication of circular DNA is an enzyme group set forth in Kaguni J M & Kornberg A. Cell. 1984, 38:183-90. Specifically, examples of the first enzyme group include an enzyme or enzyme group selected from a group consisting of an enzyme having DnaA activity, one or more types of nucleoid protein, an enzyme or enzyme group having DNA gyrase activity, single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III activity, or a combination of such enzyme or enzyme group.

The first enzyme group may be contained in the reaction solution in an amount of 1 nM to 10 µM. Preferably, the first enzyme group may be contained in the reaction solution in an amount of 1 nM to 5 µM, 1 nM to 3 µM, or 1 nM to 1.5 µM, but without being limited thereby.

The enzyme having DnaA activity is not particularly limited in its biological origin as long as it has an initiator activity that is similar to that of DnaA, which is an initiator protein of *E. coli*, and DnaA derived from *E. coli* may be preferably used. DnaA may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 50 nM to 200 nM, or 50 nM to 150 nM, but without being limited thereby.

A nucleoid protein is protein in the nucleoid. The one or more types of nucleoid protein used in the present invention is not particularly limited in its biological origin as long as it has an activity that is similar to that of the nucleoid protein of *E. coli*, and IHF derived from *E. coli*, that is, a combination of IhfA and IhfB, and HU, that is a complex of HupA and HupB, may be preferably used. IHF or HU may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme or enzyme group having DNA gyrase activity is not particularly limited in its biological origin as long as it has an activity that is similar to that of the DNA gyrase of *E. coli*, and a combination of GyrA and GyrB derived from *E. coli* may be preferably used. A combination of GyrA and GyrB may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

A single-strand binding protein (SSB) is not particularly limited in its biological origin as long as it has an activity that is similar to that of the single-strand binding protein of *E. coli*, and SSB derived from *E. coli* may be preferably used. SSB may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 50 nM to 500 nM, or 100 nM to 500 nM, but without being limited thereby.

An enzyme having DNA helicase activity is not particularly limited in its biological origin as long as it has an activity that is similar to that of the DnaB of *E. coli*, and DnaB derived from *E. coli* may be preferably used. DnaB may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme having DNA helicase loader activity is not particularly limited in its biological origin as long as it has an activity that is similar to that of the DnaC of *E. coli*, and DnaC derived from *E. coli* may be preferably used. DnaC may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme having DNA primase activity is not particularly limited in its biological origin as long as it has an activity that is similar to that of the DnaG of *E. coli*, and DnaG derived from *E. coli* may be preferably used. DnaG may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 50 nM to 500 nM, or 100 nM to 500 nM, but without being limited thereby.

An enzyme having DNA clamp activity is not particularly limited in its biological origin as long as it has an activity that is similar to that of the DnaN of *E. coli*, and DnaN derived from *E. coli* may be preferably used. DnaN may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme or enzyme group having DNA polymerase III* activity is not particularly limited in its biological origin as long as it is an enzyme or enzyme group having an activity that is similar to that of the DNA polymerase III* complex of *E. coli*, and a combination of DnaX, HolA, HolB, HolC, HolD, DnaE, DnaQ, and HolE derived from *E. coli* may be preferably used. A DNA polymerase III* complex may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 100 nM, or 1 nM to 50 nM, but without being limited thereby.

<(2) Second Enzyme Group that Catalyzes an Okazaki Fragment Maturation and Synthesizes Two Sister Circular DNAs Constituting a Catenane>

In the present invention, the two sister circular DNAs constituting a catenane are two circular DNAs synthesized by DNA replication, then joined together.

Examples of second enzyme groups that catalyze an Okazaki fragment maturation and synthesize two sister circular DNAs constituting a catenane include an enzyme or a combination of enzymes selected from a group consisting of an enzyme having RNaseH activity, an enzyme having DNA polymerase I activity, and an enzyme having DNA ligase activity.

The second enzyme group may be contained in the reaction solution in an amount of 1 nM to 10 µM. Preferably, the second enzyme group may be contained in the reaction solution in an amount of 1 nM to 5 µM, 1 nM to 3 µM, 1 nM to 1.5 µM, 1 nM to 1.0 µM, 1 nM to 500 nM, 50 nM to 200 nM, but without being limited thereby.

An enzyme having RNaseH activity is not particularly limited in its biological origin as long as it has an activity that decomposes an RNA chain in an RNA:DNA hybrid, and a RNaseH derived from E. coli may be preferably used. RNaseH may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme having DNA polymerase I activity is not particularly limited in its biological origin as long as it has an activity that is similar to DNA polymerase I of E. coli, and DNA polymerase I derived from E. coli may be preferably used. DNA polymerase I may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme having DNA ligase activity is not particularly limited in its biological origin as long as it has an activity that is similar to DNA ligase of E. coli, and DNA ligase derived from E. coli may be preferably used. DNA ligase may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

<(3) Third Enzyme Group that Catalyzes a Separation of Two Sister Circular DNAs>

An example of a third enzyme group that catalyzes a separation of two sister circular DNAs is an enzyme group set forth in Peng & Marians 1993 PNAS. Specifically, examples of the third enzyme group include an enzyme or a combination of enzymes selected from a group consisting of an enzyme having topoisomerase IV activity, an enzyme having topoisomerase III activity, and an enzyme having RecQ activity.

The third enzyme group may be contained in the reaction solution in an amount of 1 nM to 10 µM. Preferably, the third enzyme group may be contained in the reaction solution in an amount of 1 nM to 5 µM, 1 nM to 3 µM, 1 nM to 1.5 µM, 1 nM to 1.0 µM, 1 nM to 500 nM, 50 nM to 200 nM, but without being limited thereby.

An enzyme having topoisomerase IV activity is not particularly limited in its biological origin as long as it has an activity that is similar to topoisomerase IV of E. coli, and topoisomerase IV derived from E. coli which is a complex of ParC and ParE may be preferably used. Topoisomerase IV may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 100 nM, or 1 nM to 50 nM, but without being limited thereby.

An enzyme having topoisomerase III activity is not particularly limited in its biological origin as long as it has an activity that is similar to topoisomerase III of E. coli, and topoisomerase III derived from E. coli may be preferably used. Topoisomerase III may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

An enzyme having RecQ activity is not particularly limited in its biological origin as long as it has an activity that is similar to RecQ of E. coli, and RecQ derived from E. coli may be preferably used. RecQ may be contained in the reaction solution in an amount of 1 nM to 10 µM, preferably in an amount of 1 nM to 5 µM, 1 nM to 3 µM, 1 nM to 1.5 µM, 1 nM to 1.0 µM, 1 nM to 500 nM, 1 nM to 200 nM, or 1 nM to 100 nM, but without being limited thereby.

Most preferably, the following combinations may be used: for the first enzyme group, a combination of DnaA, IHF, GyrA and GyrB, SSB, DnaB and DnaC, DnaG, DnaN, and pol III* all derived from E. coli; for the second enzyme group, a combination of RNaseH, DNA polymerase I, and DNA ligase all derived from E. coli; and for the third enzyme group, a combination of topoisomerase IV, topoisomerase III and RecQ all derived from E. coli. Furthermore, the following concentrations are given as examples of preferable concentrations in case the above combinations of enzyme groups are used, without being limited thereby.

TABLE 1

| First Enzyme Group | DnaA | 100 nM |
|---|---|---|
| | IHF | 40 nM |
| | GyrA, GyrB | 50 nM |
| | SSB | 400 nM |
| | DnaB, DnaC | 20 nM |
| | DnaG | 400 nM |
| | DnaN | 40 nM |
| | PolIII* | 5 nM |
| Second Enzyme Group | RNaseH | 10 nM |
| | PolI | 50 nM |
| | Ligase | 50 nM |
| Third Enzyme Group | Topo IV | 5 nM |
| | Topo III | 50 nM |
| | RecQ | 50 nM |

The first, second and third enzyme groups given above may be those that are commercially available, or they may be extracted from microorganisms and purified as necessary. Extraction and purification of enzymes from microorganisms may be performed as necessary using means that are available to a person skilled in the art.

The reaction solution containing cell-free protein expression systems of the above mentioned enzymes may be mixed as-is with the circular DNA that constitutes a template to form a reaction mixture for amplifying circular DNA.

The cell-free protein expression system may be a cell-free translation system that comprises a total RNA containing RNA consisting of a sequence that is complementary to the base sequence of genes encoding the above enzymes, mRNA or in vitro transcription product as the template RNA, or it may be a cell-free transcription/translation system that comprises genes encoding different enzymes or expression vectors including genes that encode different enzymes as the template DNA.

<Amplification Method of Circular DNA>

The method of the present invention includes a step of forming a reaction mixture of a reaction solution containing the first and third enzyme groups and the circular DNA that constitutes a template.

The constitution of the reaction solution containing the first and third enzyme groups is not particularly limited as long as it allows DNA replication to progress, and a solution that consists of rNTP, dNTP, magnesium ion source, ATP source, etc. added to a buffer such as tris hydrochloric acid buffer and incorporating the first to third enzyme groups may be used. Further, the above reaction solution may also include additional constituents, such as a constituent for preventing or reducing the development of byproducts. Specific reaction solutions include those set forth in the Examples below.

The method of the present invention further includes a step of retaining temperature of the reaction mixture under an isothermal condition. The isothermal condition is not particularly limited as long as it allows DNA replication to progress, and the temperature may be set to a constant temperature in a range from 20° C. to 80° C. which is an optimal temperature of DNA polymerase, or a constant temperature in a range from 25° C. to 50° C., or around 30° C. The time that the temperature is retained may be set appropriately according to the target amount of amplification product of circular DNA, for example, 1 to 24 h.

The method of the present invention may include a step of purifying the amplification product of circular DNA after the step of retaining the temperature of the reaction mixture under an isothermal condition as required according to the purpose. The purification of circular DNA may be performed as necessary using means available to a person skilled in the art.

The circular DNA that had been amplified using the method of the present invention may be put to use for subsequent purposes, such as transformation, in the form of a reaction mixture after reaction as it is, or in a purified form of the reaction mixture.

<Composition or Kit for Amplifying Circular DNA>

The present invention relates to a composition for amplifying circular DNA comprising a first enzyme group that catalyzes replication of circular DNA; a second enzyme group that catalyzes an Okazaki fragment maturation and synthesizes two sister circular DNAs constituting a catenane; and a third enzyme group that catalyzes a separation of two sister circular DNAs. The composition of the present invention may include additional constituents, such as a stabilizer, a reducing agent, a reaction buffer, etc. as long as they do not inhibit the effect of the present invention.

Furthermore, the present invention also relates to a kit for amplifying circular DNA comprising a first enzyme group that catalyzes replication of circular DNA; a second enzyme group that catalyzes an Okazaki fragment maturation and synthesizes two sister circular DNAs constituting a catenane; and a third enzyme group that catalyzes a separation of two sister circular DNAs. The kit of the present invention may include a mixture of the above enzymes packed in one package, but it may also include individual enzymes packed in separate packages, or several enzymes mixed together with each mixture packed in a separate package.

Also, the present invention relates to a kit for amplifying circular DNA comprising cell-free protein expression systems of enzymes belonging to the first enzyme group that catalyzes replication of circular DNA; the second enzyme group that catalyzes an Okazaki fragment maturation and synthesizes two sister circular DNAs constituting a catenane; and the third enzyme group that catalyzes a separation of two sister circular DNAs.

The kit of the present invention may include additional components such as a condensed reaction buffer or the reaction buffer, as required by the purpose.

EXAMPLES

The present invention is explained specifically based on the EXAMPLES. Note that the present invention is not limited to the range set forth in the following Examples.

Example 1: Amplification of Circular DNA

<Ingredient and Method>

After adding the template DNA to the reaction solution of the constitution shown in Table 2 and mixing them on ice, the temperature was retained at 30° C. for 1 h., 2 h. or 3 h. by an incubator. The mixture was prepared so that the total volume for each reaction was 10 microliter. After carrying out the reaction at 30° C., the reaction product was subjected to agarose electrophoresis (0.5% 1×TAE, 150 V, 100 min., 14° C.), then DNA was detected by using SyberGreen (Takara Bio Inc.).

TABLE 2

| Reaction Buffer | |
| --- | --- |
| Tris-HCl (pH 8.0) | 20 mM |
| Dithiothreitol | 8 mM |
| potassium glutamate | 150 mM |
| Mg(OAc)$_2$ | 10 mM |
| creatine phosphate | 4 mM |
| rNTPs | Each 1 mM |
| NAD | 0.2 mM |
| ammonium sulfate | 10 mM |
| tRNA | 50 µg/mL |
| bovine serum albumin (BSA) | 0.1 mg/ml |
| dNTPs | Each 0.1 mM |
| creatine kinase | 20 µg/mL |
| Enzyme Group | |
| SSB | 400 nM |
| IHF | 40 nM |
| DnaG | 400 nM |
| DnaN | 40 nM |
| PolIII* | 5 nM |
| DnaB, DnaC | 20 nM |
| DnaA | 100 nM |
| RNaseH | 10 nM |
| Ligase | 50 nM |
| PolI | 50 nM |
| GyrA, GyrB | 50 nM |
| Topo IV | 5 nM |
| Topo III | 50 nM |
| RecQ | 50 nM |

In the table, SSB indicates SSB derived from *E. coli*, IHF indicates a combination of IhfA and IhfB derived from *E. coli*, DnaG indicates DnaG derived from *E. coli*, DnaN indicates DnaN derived from *E. coli*, PolIII* indicates DNA polymerase III* complex consisting of a combination of DnaX, HolA, HolB, HolC, HolD, DnaE, DnaQ, and HolE, DnaB indicates DnaB derived from *E. coli*, DnaC indicates DnaC derived from *E. coli*, DnaA indicates RNaseH derived from *E. coli*, Ligase indicates DNA ligase derived from *E. coli*, PolI indicates DNA polymerase I derived from *E. coli*, GyrA indicates GyrA derived from *E. coli*, GyrB indicates GyrB derived from *E. coli*, Topo IV indicates a combination of ParC and ParE derived from *E. coli*, Topo III indicates topoisomerase III derived from *E. coli*, and RecQ indicates RecQ derived from *E. coli*.

SSB was prepared by purifying an *E. coli* strain expressing SSB by steps that include ammonium sulfate precipitation and ion-exchange column chromatography.

IHF was prepared by purifying an *E. coli* strain coexpressing IhfA and IhfB by steps that include ammonium sulfate precipitation and affinity column chromatography.

DnaG was prepared by purifying an *E. coli* strain expressing DnaG by steps that include ammonium sulfate precipitation and anion-exchange column chromatography and gel filtration column chromatography.

DnaN was prepared by purifying an *E. coli* strain expressing DnaN by steps that include ammonium sulfate precipitation and anion-exchange column chromatography.

PolIII* was prepared by purifying an *E. coli* strain coexpressing DnaX, HolA, HolB, HolC, HolD, DnaE, DnaQ, and HolE by steps that include ammonium sulfate precipitation, affinity column chromatography and gel filtration column chromatography.

DnaB and DnaC were prepared by purifying an *E. coli* strain coexpressing DnaB and DnaC by steps that include ammonium sulfate precipitation, affinity column chromatography and gel filtration column chromatography.

DnaA was prepared by purifying an *E. coli* strain expressing DnaA by steps that include ammonium sulfate precipitation, dialysis precipitation, and gel filtration column chromatography.

GyrA and GyrB were prepared by purifying a mixture of an *E. coli* strain expressing GyrA and an *E. coli* strain expressing GyrB by steps that include ammonium sulfate precipitation, affinity column chromatography and gel filtration column chromatography.

Topo IV was prepared by purifying a mixture of an *E. coli* strain expressing ParC and an *E. coli* strain expressing ParE by steps that include ammonium sulfate precipitation, affinity column chromatography and gel filtration column chromatography.

Topo III was prepared by purifying an *E. coli* strain expressing Topo III by steps that include ammonium sulfate precipitation, and affinity column chromatography.

RecQ was prepared by purifying an *E. coli* strain expressing RecQ by steps that include ammonium sulfate precipitation, affinity column chromatography and gel filtration column chromatography.

Commercially available enzymes derived from *E. coli* were used for RNaseH, Ligase and PolI (Takara Bio Inc.).

As the template DNA, a 9.6 kb circular DNA (circular DNA having a replication origin sequence oriC, kanamycin resistance (Km)), a 80 kb long chain circular DNA (circular DNA having a replication origin sequence oriC, kanamycin resistance (Km)), a 200 kb long chain circular DNA (circular DNA having a replication origin sequence oriC, kanamycin resistance (Km)) or a DNA cyclized by in vitro ligation were used.

The 9.6 kb circular DNA and the 80 kb and 200 kb long chain circular DNAs were prepared by in vivo recombination in *E. coli* cells. Specifically, an in vivo recombination was performed using *E. coli* expressing a recombination protein group of λ phage to prepare circular DNA of a desired length including a kanamycin resistance cassette and a region in the *E. coli* chromosome that includes oriC.

Figure 2:
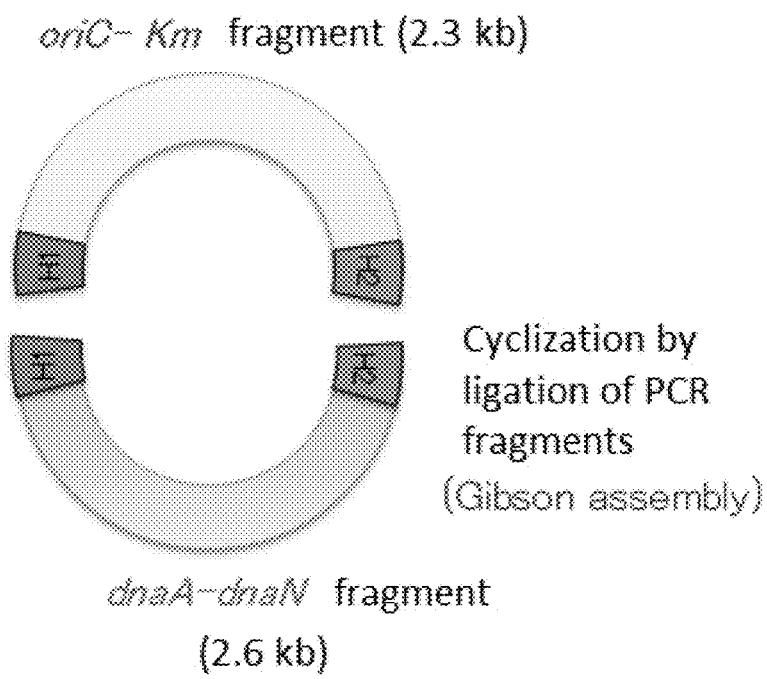
FIG. 2 shows the structure of DNA cyclized by in vitro ligation using the Gibson Assembly method.

A method for preparing circular DNA by in vitro ligation is shown in FIG. 2. Specifically, a PCR fragment (2.3 kb) having a replication origin sequence oriC and a region having kanamycin resistance (Km) was ligated with a PCR fragment having sequences of the dnaA gene and dnaN gene (hereinafter referred to as dnaA-dnaN fragment) (2.6 kb) by a reaction using the Gibson assembly method. The two PCR fragments were ligated through homologous sequences of 20 bases (referred to as H1, H2) attached to both ends to form a circular structure. The reaction was performed by mixing the above two PCR fragments with the Gibson Assembly Master Mix (NEB) and letting the mixture react at 50° C. for 15 min. After the reaction, 0.1 microliter of the reaction solution (1 microliter of the reaction solution diluted to 10 folds) was used as the template DNA to be added directly to an amplification reaction system of 10 microliters (constitution of Table 2), and the mixture was reacted at 30° C. for 1 h.

Figure 3:
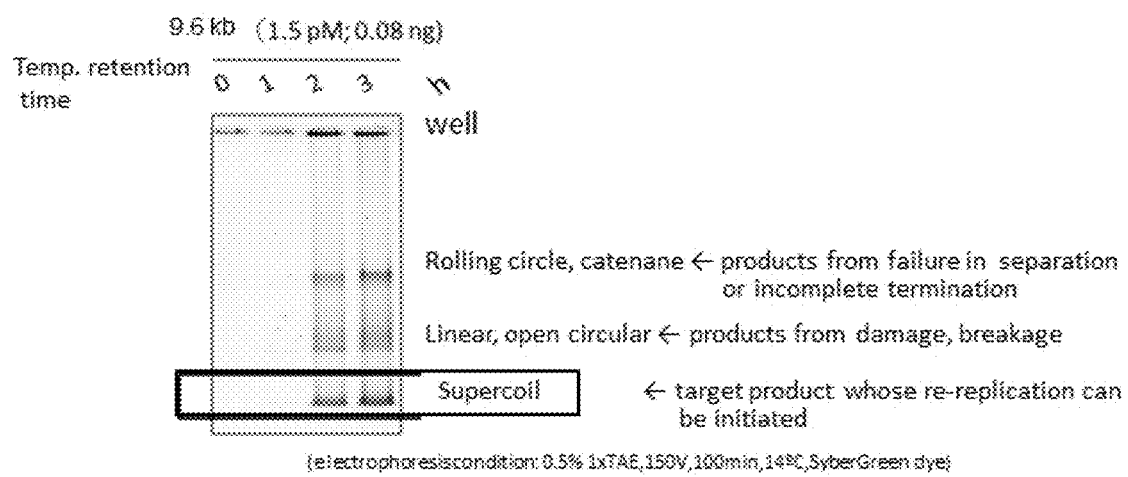
FIG. 3 shows the detection result of the amplification product at each reaction time in a case in which a circular DNA of 9.6 kb was used as a template, the detection result obtained by using SyberGreen after subjecting the product to agarose electrophoresis.

<Result 1> Case Using 9.6 kb Circular DNA (0.08 ng, about $10^7$ of Circular Molecules) as Template FIG. 3 shows the detection result of the amplification product using SyberGreen.

The circular DNA amplification product having a supercoil structure (indicated by a black box) was confirmed as well as a byproduct (a reaction intermediate).

The amplification amount of circular DNA was obtained by transforming an *E. coli* DH5α strain using the solution after reaction as it was, cultivating the strain in a kanamycin-containing agar, and measuring the number of colonies, and the result is shown in Table 3. A reaction solution whose temperature had been retained for 0 h. was used as the control.

TABLE 3

|  | Temperature Retention Time | |
| --- | --- | --- |
|  | 0 h. | 3 h. |
| Transformation Product (no. of colonies) | 9 | $5.4 \times 10^4$ |

The method of the present invention enabled a 9.6 kb circular DNA to be amplified to 6,000 folds of circular DNA.

<Result 2> Case Using 80 kb and 200 kb Long Chain Circular DNAs as Templates

Figure 4:
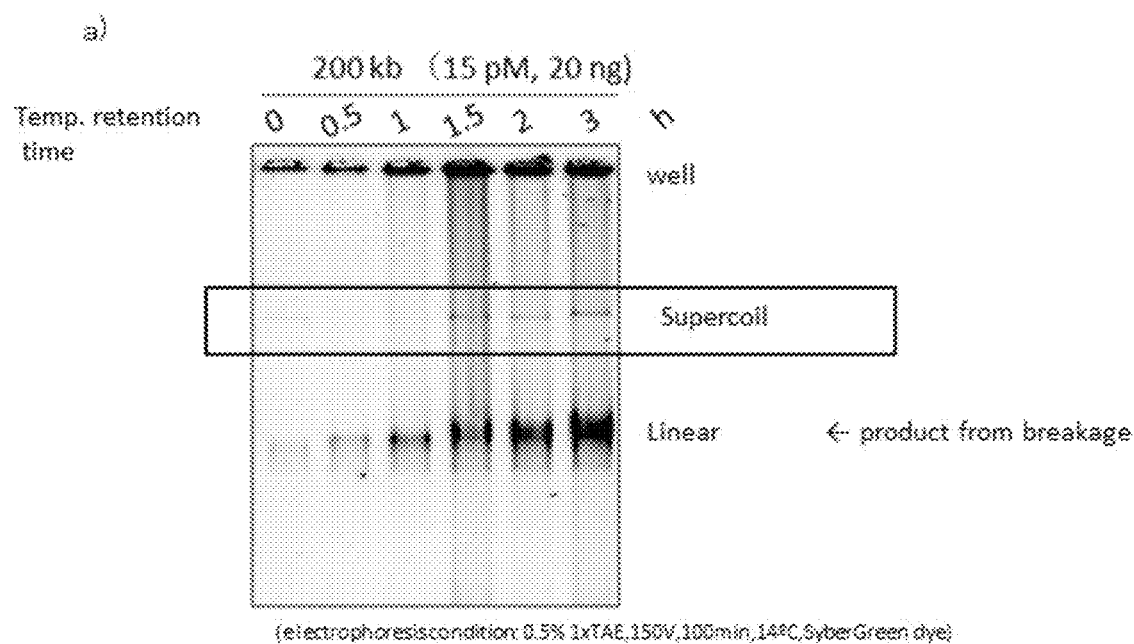
FIG. 4 shows the detection results of the amplification products in a case in which long chain circular DNAs of 200 kb and 80 kb were used as templates, the detection result obtained by using SyberGreen after subjecting the product to agarose electrophoresis.
Figure 4:
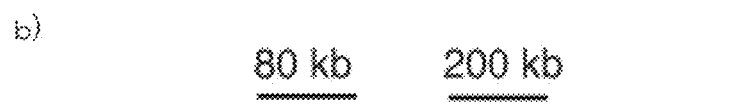

FIG. 4 shows the detection result of an amplification product obtained using SyberGreen.

The circular DNA amplification product having a supercoil structure (indicated by a black box or arrow) was confirmed.

The method of the present invention showed that a good amplification product may be obtained even when long circular DNAs of 80 kb or 200 kb are used as templates.

<Result 3> Case Using DNA Cyclized by In Vitro Ligation as Template

Figure 5:
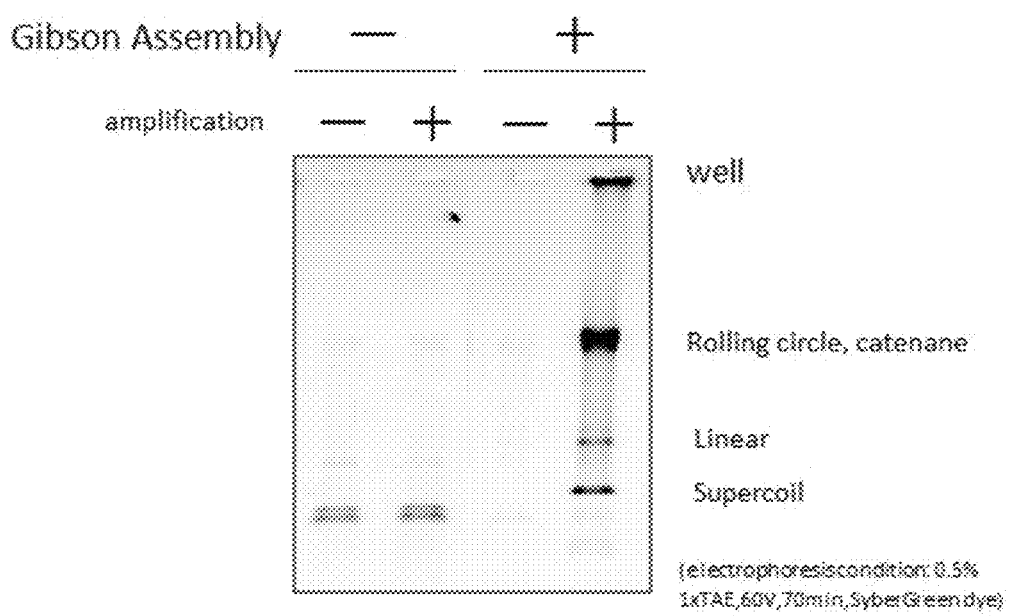
FIG. 5 shows the detection result of the amplification product in a case in which DNA cyclized by in vitro ligation using the Gibson Assembly method was used as a template, the detection result obtained by using SyberGreen after subjecting the product to agarose electrophoresis.

FIG. 5 shows the detection result of an amplification product detected by using SyberGreen.

The method of the present invention showed that a good amplification product may be obtained even when DNA cyclized by in vitro ligation is used as the template.

The amplification amount of circular DNA was obtained by transforming an *E. coli* DH5α strain using the solution after reaction as it was, cultivating the strain in a kanamycin-containing agar, and measuring the number of colonies, and its result is shown in Table 4. A sample that was not subjected to amplification was used as the control.

TABLE 4

| Amplification Reaction | − | + |
| --- | --- | --- |
| Transformation Product (no. of colonies) | $3.2 \times 10^2$ | $6.6 \times 10^5$ |

The method of the present invention enabled the DNA cyclized by using the Gibson Assembly method to be amplified to 2,000 folds in circular DNA.

Example 2: Amplification of Circular DNA from Few Template Molecules

The 9.6 kb circular DNA shown in Example 1 was used to perform amplification similar to Example 1.

(2-1) Analysis of Amplification Efficiency

Figure 6:
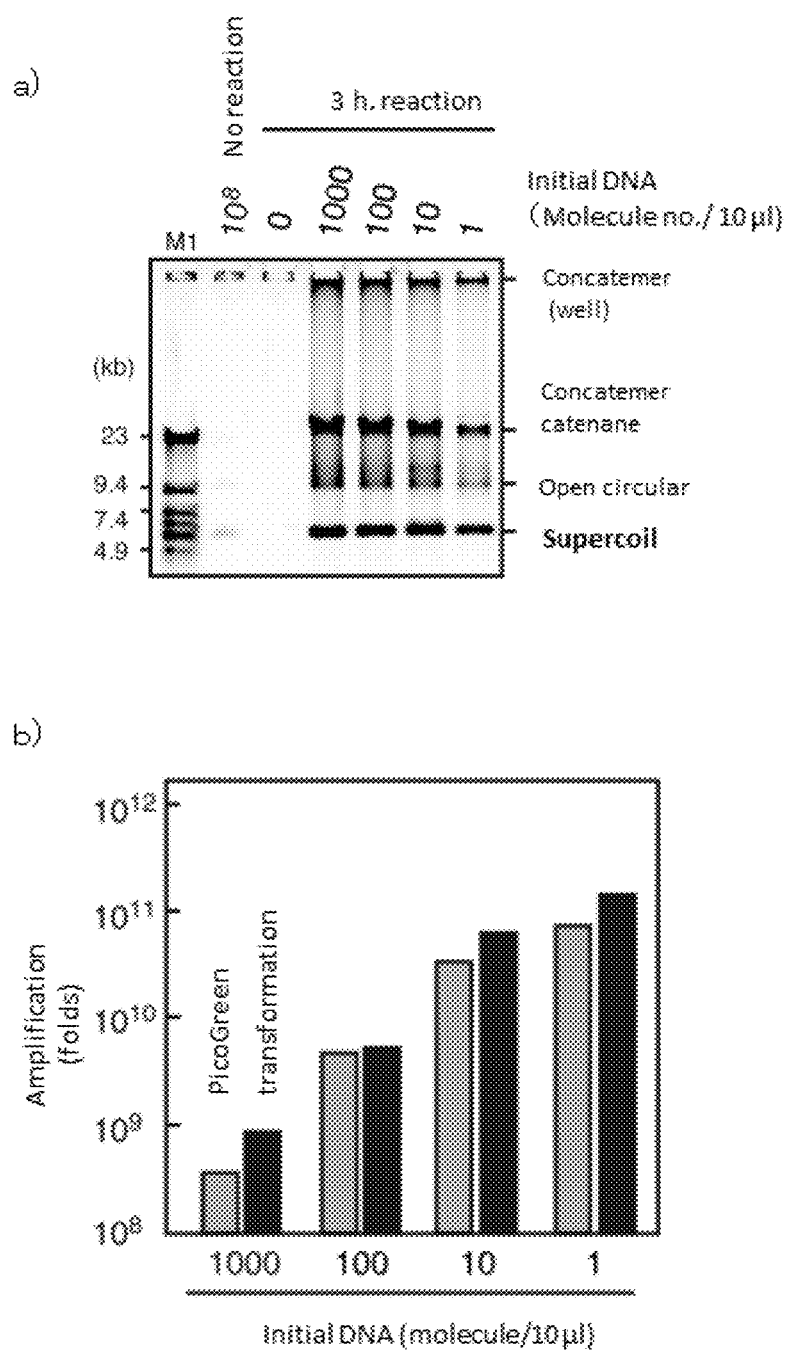
FIG. 6 shows the result of the amplification experiment in which a circular DNA of 9.6 kb in a minute amount (at a level of one molecule) was used as a template.

To 10 µl of an amplification reaction solution (Example 1, Table 2) was added a 9.6 kb circular DNA so that the solution contained 1 to 1,000 circular molecules, then the temperature of the solution was retained at 30° C. for 3 h. to let amplification progress. The reaction product was subjected to 0.5% agarose electrophoresis and stained with SybrGreen (Takara Bio Inc.) to detect amplified DNA (FIG. 6a). Furthermore, the total amount of DNA of the amplification product was quantified by using the PicoGreen Detection kit (ThermoFisher) (FIG. 6b: PicoGreen Method). The amplification amount of the circular DNA molecule was quantified by directly transforming the amplification product to E. coli, and calculating the number of kanamycin resistance colonies (FIG. 6b: Transformation). The quantification result was used to obtain the level of amplification against the initial DNA amount (amplification), and the result is shown in the graph.

The above result made evident that a single molecule of circular DNA constituting the template DNA may be amplified to about $10^{11}$ molecules by a mere 3 h. of isothermal reaction (amplification of about 100 billion folds).

(2-2) Analysis of Doubling Time

Figure 7:
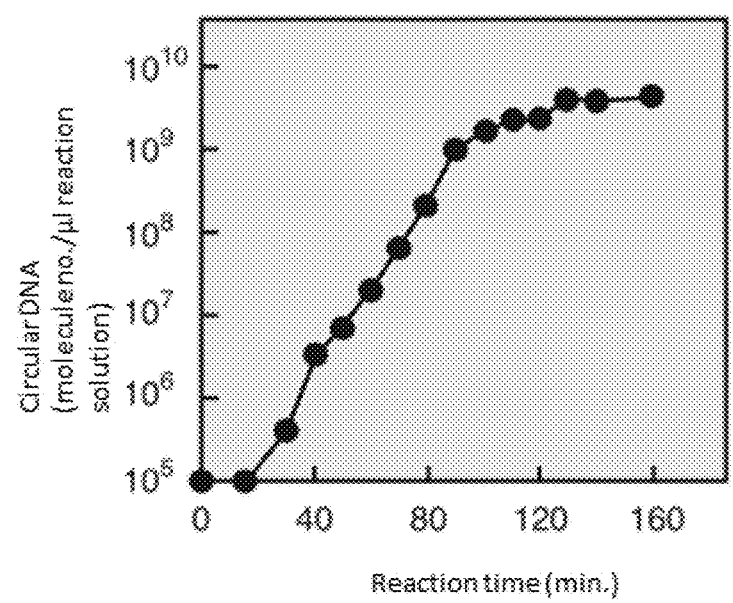
FIG. 7 is a graph that depicts the number of amplified circular DNA molecules corresponding to the amplification time in a case in which a circular DNA of 9.6 kb was used as a template.

To 80 µl of amplification reaction solution (Example 1, Table 2), the above circular DNA was added and the temperature of the solution was retained at 30° C. to let amplification progress. Circular DNA was added so that every 1 µl of the reaction solution contained $10^5$ molecules. The number of amplified circular DNA was quantified by sampling the solution over time, directly transforming the sample to E. coli, and calculating the number of kanamycin resistance colonies (FIG. 7).

It was confirmed from the above result that the doubling time of 9.6 kb circular DNA molecules is about 5 min.

Example 3: Amplification of Single, Circular DNA Clone from Mixture

Amplification of a single, circular DNA clone was performed from a mixture of a 9.6 kb circular DNA and a 12.0 kb circular DNA shown in Example 1 (circular DNA having a replication origin sequence oriC, kanamycin resistance (Km)).

The 12.0 kb circular DNA was prepared by in vivo recombination in E. coli cells. Specifically, in vivo recombination was performed using E. coli expressing a recombination protein group of λ phage to prepare circular DNA of a desired length including oriC and a cassette consisting of a kanamycin resistance gene and some region in the E. coli chromosome.

Figure 8:
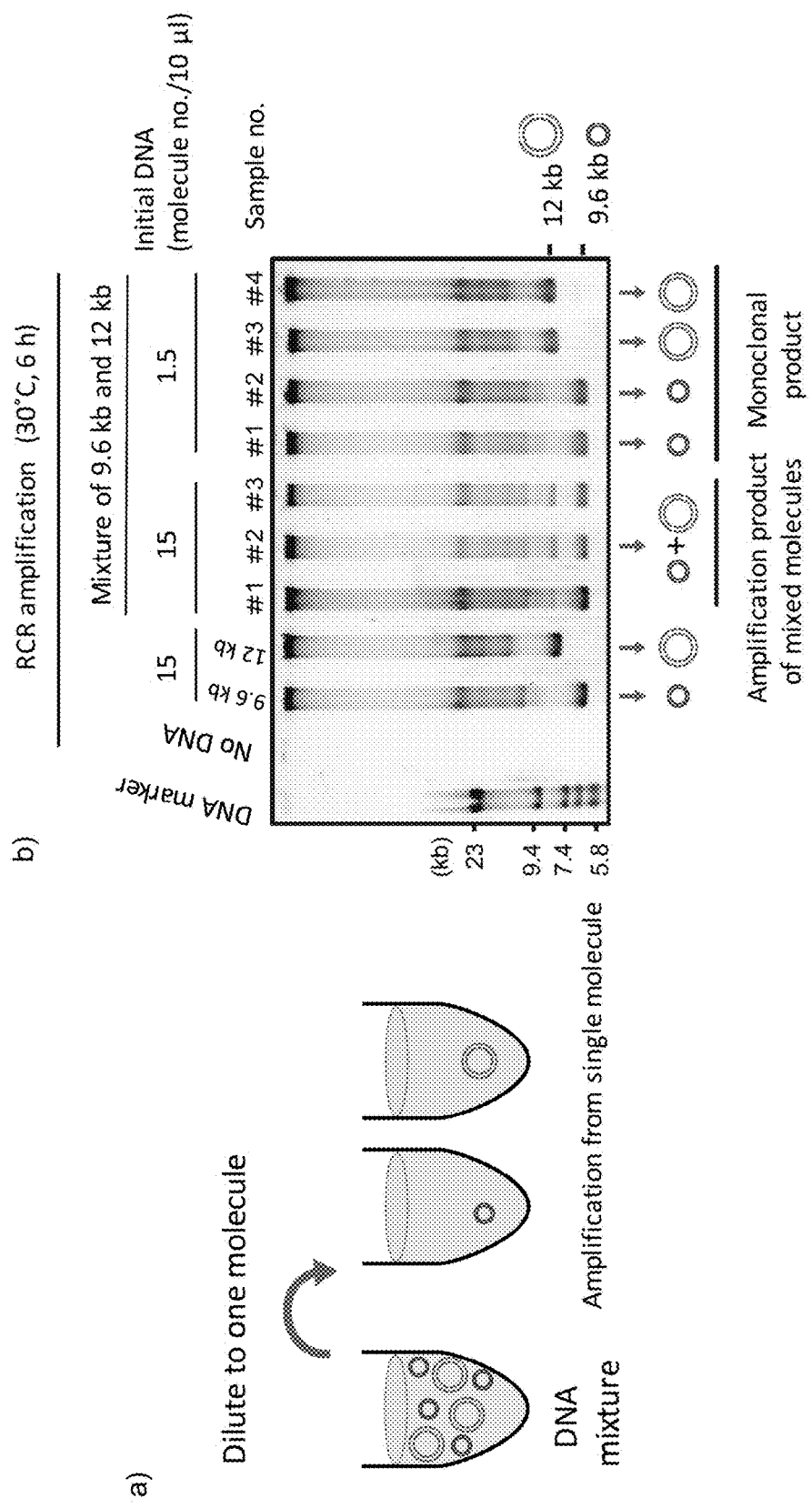
FIG. 8 is a diagram showing the amplification test result of a single circular DNA clone in a mixture.

To 10 µl of the amplification reaction solution (Example 1, Table 2), a mixture of the above two types of circular DNAs was added so that the reaction solution would contain each type of circular DNA in a number of 15 molecules or diluted to 1.5 molecules, then the temperature was retained at 30° C. for 6 h. to let amplification progress. From the reaction product, the amplification DNA was detected by subjecting the product to 0.5% agarose electrophoresis and staining it with SybrGreen (Takara Bio Inc.) (FIG. 8).

As a result, the clone of just one of the two types of circular DNAs was amplified for each reaction sample in the reaction solution diluted to 1.5 molecules of circular DNA. This shows that, even if the template DNA is a mixture, it is possible to amplify a single, circular DNA clone by diluting the mixture to a level of 1 molecule in the reaction solution.

Example 4: Passage Amplification

The passage amplification of circular DNA was tested using lacZ circular DNA.

Figure 9:
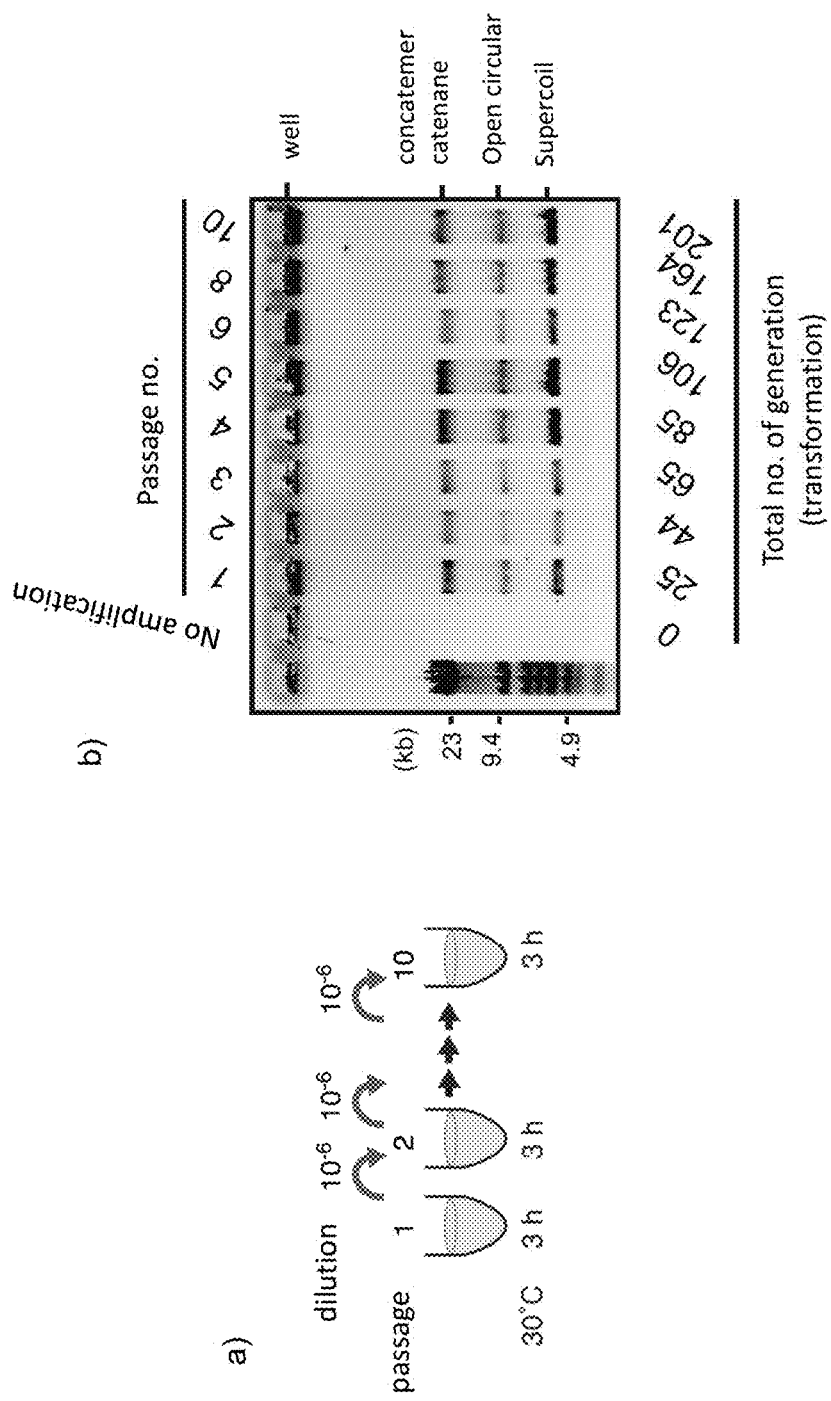
FIG. 9 is a diagram showing the passage amplification test result of circular DNA.

The lacZ circular DNA (9.0 kb) was prepared by ligating a double strand DNA fragment including oriC (1.0 kb), a double strand DNA fragment including kanamycin resistance gene (Km) (4.6 kb) and a double strand DNA fragment including lacZ (β-galactosidase) gene (3.4 kb). To 10 µl of amplification reaction solution (Example 1, Table 2) was added lacZ circular DNA so that the solution contains 1,000 molecules of the DNA, then the temperature of the solution was retained at 30° C. for 3 h. to let amplification progress. This constitutes one passage. The amplification reaction product from the previous passage number was diluted to $10^5$ folds, and 1 µl of this was added to the new amplification reaction solution to induce a similar reaction to constitute the next passage amplification. The passage amplification was repeated 10 times. The amplification product of each passage was detected by being subjected to 0.5% agarose electrophoresis and stained with SybrGreen (Takara Bio Inc.) (FIG. 9). A part of the amplification product was transformed to E. coli and the level of DNA amplification was quantified by the number of kanamycin resistance colonies, then this number was used to calculate the number of generations the exponential amplification was repeated which constitutes the total number of generations.

It was consequently recognized that the amplification of circular DNA was progressing efficiently even after 10 passages. As the result of Example 2 (FIG. 7) shows, when the circular DNA amplifies to a certain extent, the amplification rate levels off due to the exhaustion of the substrate or enzyme. Meanwhile, the result of the present Example shows that it is possible to semipermanently repeat an exponential amplification of circular DNA by passaging a part of the amplification reaction product in the new reaction solution. In other words, the method of the present invention is a method which enables amplification of circular DNA to be performed similarly to the passage amplification of cells.

Example 5: Incidence of Replication Error in Amplification

Because the template circular DNA in Example 4 includes lacZ genes, the colony that expresses lacZ genes properly (lacZ⁺) becomes blue since it can decompose X-gal and the colony whose lacZ gene does not function properly due to mutation introduced by an error in replication (lacZ⁻) becomes white since it cannot decompose X-gal when E. coli that had been transformed by the above circular genes is cultivated in the X-gal plate. In other words, it is possible to judge the replication error in the amplified circular DNA by the color that the E. coli that had been transformed by the aforementioned circular genes expresses in the X-gal plate.

The amplification reaction product of each passage sample was directly transformed to E. coli, and cultivated on the X-gal plate to obtain the lacZ⁻ incidence. The lacZ⁻ incidence and the total number of generation obtained in Example 4 were used to calculate the error incidence of one generation of replication cycle according to the method of Barnes (Barnes W M Gene. 1992, 112, 29-35). The result is shown in Table 5 below.

TABLE 5

| Passage Number | Total Number of Generations | lacZ⁻ colony incidences (%) | Error incidence (per base) |
|---|---|---|---|
| 1 | 25 | <0.045 | $<3.7 \times 10^{-8}$ |
| 2 | 44 | <0.074 | $<3.4 \times 10^{-8}$ |

TABLE 5-continued

| Passage Number | Total Number of Generations | lacZ⁻ colony incidences (%) | Error incidence (per base) |
|---|---|---|---|
| 5 | 106 | 0.1 | $1.9 \times 10^{-8}$ |
| 10 | 201 | 0.093 | $0.93 \times 10^{-8}$ |

The above result shows that replication errors occur at approximately one position per 100 million bases (an average of $1.4 \times 10^{-8}$ errors per base). This is about the same as the mutation rate in the cell (strains without mismatch correction system), and about 10 thousand times more accurate than Taq polymerase.

The invention claimed is:

1. A kit for amplifying circular DNA comprising a mixture of the following three enzyme groups in a single container, wherein each of the enzymes is a recombinant enzyme:
   (a) a first enzyme group that catalyzes replication of circular DNA;
   (b) a second enzyme group that catalyzes an Okazaki fragment maturation and synthesizes two sister circular DNAs constituting a catenane; and
   (c) a third enzyme group that catalyzes a separation of two sister circular DNAs, which is an enzyme group comprising at least two enzymes selected from a group consisting of an enzyme having topoisomerase III activity, an enzyme having topoisomerase IV activity, and an enzyme having RecQ activity.

2. The kit according to claim 1, wherein
   the first enzyme group comprises a combination of an enzyme having DnaA activity, one or more types of nucleoid protein, an enzyme or enzyme group having DNA gyrase activity, single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III activity; and wherein
   the second enzyme group comprises a combination of an enzyme having DNA polymerase I activity, and an enzyme having DNA ligase activity.

3. The kit according to claim 1, further comprising tRNA.

4. The kit according to claim 2, further comprising tRNA.

5. The kit according to claim 1, further comprising potassium glutamate.

6. The kit according to claim 2, further comprising potassium glutamate.

7. The kit according to claim 3, further comprising potassium glutamate.

8. A kit for exponentially amplifying circular DNA by repeating replication cycles, comprising a mixture of the following three enzyme groups in a single container, wherein each of the enzymes is a recombinant enzyme:
   (a) a first enzyme group that catalyzes replication of circular DNA;
   (b) a second enzyme group that catalyzes an Okazaki fragment maturation and synthesizes two sister circular DNAs constituting a catenane; and
   (c) a third enzyme group that catalyzes a separation of two sister circular DNAs.

9. A kit for amplifying circular DNA comprising a mixture of the following three enzyme groups in a single container, wherein each of the enzymes is a recombinant enzyme:
   (a) a first enzyme group that catalyzes replication of circular DNA;
   (b) a second enzyme group that catalyzes an Okazaki fragment maturation and synthesizes two sister circular DNAs constituting a catenane; and
   (c) a third enzyme group that catalyzes a separation of two sister circular DNAs, and
   an additional constituent, wherein
   said additional constituent is a constituent which describes a method of exponentially amplifying circular DNA by repeating replication cycles in a reaction mixture composed of a reaction solution containing said first, second and third enzyme groups and circular DNA that constitutes a template.

10. The kit of claim 1, further comprising rNTPs and dNTPs in the same or a separate container.

11. The kit of claim 8, further comprising rNTPs and dNTPs in the same or a separate container.

12. The kit of claim 9, further comprising rNTPs and dNTPs in the same or a separate container.

13. The kit of claim 1, wherein the mixture is in solution.

14. The kit of claim 8, wherein the mixture is in solution.

15. The kit of claim 9, wherein the mixture is in solution.

* * * * *